United States Patent
Simmons

(10) Patent No.: US 12,036,373 B2
(45) Date of Patent: Jul. 16, 2024

(54) CATHETER WITH FLARING TIP

(71) Applicant: Bard Peripheral Vascular, Inc., Tempe, AZ (US)

(72) Inventor: Brandon David Simmons, Tempe, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 651 days.

(21) Appl. No.: 17/055,721

(22) PCT Filed: May 17, 2019

(86) PCT No.: PCT/US2019/032965
§ 371 (c)(1),
(2) Date: Nov. 16, 2020

(87) PCT Pub. No.: WO2019/222687
PCT Pub. Date: Nov. 21, 2019

(65) Prior Publication Data
US 2021/0205584 A1 Jul. 8, 2021

Related U.S. Application Data

(60) Provisional application No. 62/673,632, filed on May 18, 2018, provisional application No. 62/673,628, filed on May 18, 2018.

(51) Int. Cl.
*A61M 25/01* (2006.01)
*A61K 51/12* (2006.01)
(Continued)

(52) U.S. Cl.
CPC ..... *A61M 25/0147* (2013.01); *A61K 51/1241* (2013.01); *A61M 5/1785* (2013.01);
(Continued)

(58) Field of Classification Search
CPC .......... A61M 25/0147; A61M 25/0021; A61M 25/0082; A61M 2025/09075; A61M 2025/0073; A61M 2025/0076
See application file for complete search history.

(56) References Cited

U.S. PATENT DOCUMENTS

| | | | |
|---|---|---|---|
| 4,313,440 A | 2/1982 | Ashley | |
| 5,192,286 A * | 3/1993 | Phan | ..................... A61F 2/0105 606/1 |

(Continued)

FOREIGN PATENT DOCUMENTS

| | | |
|---|---|---|
| CN | 102665608 A | 9/2012 |
| CN | 103702708 A | 4/2014 |

(Continued)

OTHER PUBLICATIONS

Notice of Allowance dated Sep. 5, 2023, pertaining to Japanese Patent Application 2020-564539.
(Continued)

*Primary Examiner* — Jason E Flick
*Assistant Examiner* — Adam J. Cermak
(74) *Attorney, Agent, or Firm* — Dinsmore & Shohl LLP

(57) ABSTRACT

In the present disclosure, embodiments include flaring tip microcatheters, methods of deploying flaring tip microcatheters, and embolization treatment methods. The flaring tip microcatheter may include a hollow shaft having a shaft lumen defined therein, a core disposed within the shaft lumen, and a tip including at least two petals affixed to a distal end of the core, the at least two petals including at least two wires wherein the core is hollow and defines a core lumen. The at least two wires may be configured to pull the at least two petals to form a flared configuration of the tip. The flared configuration of the tip may allow for laminar flow of a therapeutic agent distally from the tip.

11 Claims, 9 Drawing Sheets

(51) Int. Cl.
| | |
|---|---|
| *A61M 5/178* | (2006.01) |
| *A61M 5/19* | (2006.01) |
| *A61M 5/31* | (2006.01) |
| *A61M 5/315* | (2006.01) |
| *A61M 25/00* | (2006.01) |
| *A61M 25/09* | (2006.01) |
| *A61N 5/10* | (2006.01) |
| *G16H 20/17* | (2018.01) |

(52) U.S. Cl.
CPC ............ *A61M 5/19* (2013.01); *A61M 5/3129* (2013.01); *A61M 5/31571* (2013.01); *A61M 25/0021* (2013.01); *A61M 25/09* (2013.01); *A61N 5/1002* (2013.01); *A61N 5/1007* (2013.01); *G16H 20/17* (2018.01); *A61M 2025/0042* (2013.01); *A61M 2025/09075* (2013.01); *A61M 2025/09166* (2013.01); *A61M 2205/14* (2013.01); *A61M 2205/3331* (2013.01); *A61M 2205/3334* (2013.01); *A61M 2205/50* (2013.01); *A61M 2206/11* (2013.01); *A61N 2005/1019* (2013.01)

(56) References Cited

U.S. PATENT DOCUMENTS

| | | | |
|---|---|---|---|
| 5,203,772 A * | 4/1993 | Hammerslag ... | A61M 25/09025 604/95.04 |
| 5,478,323 A | 12/1995 | Westwood et al. | |
| 5,496,284 A | 3/1996 | Waldenburg | |
| 5,571,085 A * | 11/1996 | Accisano, III .... | A61M 25/0136 604/95.01 |
| 6,152,913 A | 11/2000 | Feith et al. | |
| 6,293,958 B1 * | 9/2001 | Berry ................ | A61M 25/0075 606/191 |
| 6,508,807 B1 | 1/2003 | Peters | |
| 6,606,370 B1 | 8/2003 | Kasprowicz | |
| 6,723,074 B1 | 4/2004 | Halseth | |
| 7,338,466 B2 * | 3/2008 | Hart ..................... | A61M 25/04 604/93.01 |
| 7,713,239 B2 | 5/2010 | Uber, III et al. | |
| 8,500,775 B2 * | 8/2013 | Chomas ........... | A61B 17/12172 606/200 |
| 8,671,817 B1 * | 3/2014 | Bogusky .................. | D04C 3/48 87/35 |
| 8,696,698 B2 * | 4/2014 | Chomas ................... | A61F 2/014 606/200 |
| 8,696,699 B2 * | 4/2014 | Chomas ................... | A61F 2/014 606/200 |
| 9,662,458 B2 * | 5/2017 | Schatz ............. | A61M 25/0108 |
| 2001/0021826 A1 | 9/2001 | Winkler | |
| 2003/0201639 A1 | 10/2003 | Korkor | |
| 2004/0059288 A1 * | 3/2004 | Webler ............. | A61M 25/0147 604/95.04 |
| 2004/0111078 A1 | 6/2004 | Miyahara | |
| 2004/0258614 A1 | 12/2004 | Line et al. | |
| 2005/0085685 A1 * | 4/2005 | Barbut ............. | A61B 17/12109 600/16 |
| 2006/0033334 A1 | 2/2006 | Weber et al. | |
| 2006/0091329 A1 | 5/2006 | Eguchi | |
| 2006/0253063 A1 | 11/2006 | Schweikert | |
| 2006/0293552 A1 | 12/2006 | Polsinelli et al. | |
| 2007/0129591 A1 | 6/2007 | Yanke et al. | |
| 2007/0141339 A1 | 6/2007 | Song et al. | |
| 2008/0058719 A1 | 3/2008 | Edwards et al. | |
| 2008/0103564 A1 | 5/2008 | Burkinshaw et al. | |
| 2008/0200747 A1 | 8/2008 | Wagner et al. | |
| 2009/0018498 A1 * | 1/2009 | Chiu ..................... | A61M 25/10 604/97.02 |
| 2009/0092677 A1 | 4/2009 | Richard | |
| 2009/0233586 A1 | 9/2009 | Diodati et al. | |
| 2010/0084585 A1 | 4/2010 | Prosser | |
| 2010/0145306 A1 * | 6/2010 | Mickley ............ | A61M 25/0084 604/529 |
| 2011/0144576 A1 * | 6/2011 | Rothe ............... | A61M 25/0136 604/95.04 |
| 2012/0123327 A1 * | 5/2012 | Miller ............... | A61M 25/0136 604/95.04 |
| 2012/0190976 A1 | 7/2012 | Kleinstreuer | |
| 2012/0201726 A1 | 8/2012 | Pearcy et al. | |
| 2012/0316429 A1 * | 12/2012 | Schmidt ........... | G01R 33/34084 600/585 |
| 2013/0165899 A1 | 6/2013 | Haueter et al. | |
| 2013/0317277 A1 | 11/2013 | Lerner | |
| 2014/0046295 A1 | 2/2014 | Uber, III et al. | |
| 2014/0128844 A1 * | 5/2014 | Kornowski ....... | A61M 25/0009 604/509 |
| 2014/0163302 A1 | 6/2014 | Fox et al. | |
| 2014/0207178 A1 * | 7/2014 | Chomas .................. | A61F 2/014 606/200 |
| 2014/0236093 A1 | 8/2014 | Eggert et al. | |
| 2014/0257233 A1 | 9/2014 | Cowan | |
| 2015/0273089 A1 | 10/2015 | Gray | |
| 2015/0273181 A1 * | 10/2015 | Leeflang ............. | A61M 25/005 606/41 |
| 2015/0285282 A1 | 10/2015 | Weitz et al. | |
| 2016/0158497 A1 * | 6/2016 | Tran .................. | A61M 25/0147 604/95.04 |
| 2016/0325047 A1 | 11/2016 | Vedrine et al. | |
| 2016/0331853 A1 | 11/2016 | Taub | |
| 2016/0331998 A1 | 11/2016 | Hoffman et al. | |
| 2017/0065732 A1 | 3/2017 | Srinivas et al. | |
| 2017/0106170 A1 * | 4/2017 | Hsueh ............... | A61M 25/0147 |
| 2017/0120032 A1 | 5/2017 | Miyazaki et al. | |
| 2017/0151357 A1 | 6/2017 | Cade | |
| 2017/0189569 A1 | 7/2017 | Souresrafil et al. | |
| 2017/0238951 A1 | 8/2017 | Yang et al. | |
| 2017/0304151 A1 | 10/2017 | Van Den Berg et al. | |

FOREIGN PATENT DOCUMENTS

| | | |
|---|---|---|
| CN | 107206207 A | 9/2017 |
| CN | 107376093 A | 11/2017 |
| DE | 3035290 A1 | 4/1982 |
| DE | 4318101 A1 | 12/1994 |
| EP | 2179758 A2 | 4/2010 |
| FR | 2917981 A1 | 1/2009 |
| JP | 2006017660 A | 1/2006 |
| JP | 2006507032 A | 3/2006 |
| JP | 2013512735 A | 4/2013 |
| JP | 2014200361 A | 10/2014 |
| WO | 2007008511 A2 | 1/2007 |
| WO | 2009039203 A2 | 3/2009 |
| WO | 2011014562 A1 | 2/2011 |
| WO | 2011068924 A1 | 6/2011 |
| WO | 2012006555 A1 | 1/2012 |
| WO | 2012118687 A1 | 9/2012 |
| WO | 2013153722 A1 | 10/2013 |
| WO | 2014165058 A1 | 10/2014 |
| WO | 2016049685 A1 | 4/2016 |
| WO | 2016161346 A1 | 10/2016 |
| WO | 2017053398 A1 | 3/2017 |
| WO | 2017157974 A1 | 9/2017 |
| WO | 2019006099 A1 | 1/2019 |
| WO | 2019222699 A1 | 1/2019 |
| WO | 2019222680 A1 | 11/2019 |
| WO | 2019222700 A1 | 11/2019 |
| WO | 2019222713 A1 | 11/2019 |

OTHER PUBLICATIONS

Chiesa, C. et al.; A dosimetric treatment planning strategy in radioembolization of hepatocarcinoma with 90Y glass microspheres; The Quarterly Journal of Nuclear Medicine and Molecular Imaging, vol. 56, No. 6; Dec. 1, 2012.

Chiesa, C. et al.; Radioembolization of hepatocarcinoma with 90Y glass microspheres: development of an individualized treatment planning strategy based on dosimetry and radiobiology; European Journal of Nuclear Medicine and Molecular Imaging, Springer Verlag, Heidelberg, DE; vol. 42; No. 11; Jun. 27, 2015.

(56) References Cited

OTHER PUBLICATIONS

Spreafico, C. et al.; The dosimetric importance of the number of 90Y microspheres in liver transarterial radioembolizaiton (TARE); European Journal of Nuclear Medicine and Molecular Imaging, Springer Verlag, Heidelberg, DE; vol. 41, No. 4; Jan. 30, 2014.
International Search Report and Written Opinion dated Aug. 1, 2019 pertaining to International Application No. PCT/US2019/032983.
International Search Report and Written Opinion dated Dec. 13, 2019 pertaining to International Application No. PCT/US2019/032987.
International Search Report and Written Opinion dated Oct. 16, 2019 pertaining to International Application No. PCT/US2019/032955.
International Search Report and Written Opinion dated Jul. 23, 2019 pertaining to International Application No. PCT/US2019/032950.
International Search Report and Written Opinion dated Jul. 26, 2019 pertaining to International Application No. PCT/US2019/032965.
International Search Report and Written Opinion dated Jul. 29, 2019 pertaining to International Application No. PCT/US2019/032954.
International Search Report and Written Opinion dated Aug. 7, 2019 pertaining to International Application No. PCT/US2019/032986.
Arepally, A.; Quantification and Reduction of Reflux during Embolotherapy Using an Antireflux Catheter and Tantalum Microspheres: Ex Vivo Analysis; J Vasc Interv Radiol; 2013; 24:575-580.
Chung, J. et al.; Novel use of the Surefire antireflux device in subtotal splenic embolization; Journal of Vascular Surgery Cases; Dec. 1, 2015; pp. 242-245; vol. 1, No. 4.
Ho, S. et al; Clinical evaluation of the partition model for estimating radiation doses from yttrium-90 microspheres in the treatment of hepatic cancer; European Journal of Nuclear Medicine, Springer, Berlin, Heidelberg, DE: vol. 24. No. 3; Mar. 1, 1997.
Hospital Clinics et al.; Y-90 MicroSpheres (SIRSpheres) for treatment of hepatocellular carcinoma; Mar. 1, 2017.
Morshedi, M. et al.; Yttrium-90 Resin Microsphere Radioembolization Using an Antireflux Catheter: An Alternative to Traditional Coil Embolization for Nontarget Protection; Cardiovasc Intervent Radiol; 2015; 38:381-38; Springer.
Sirtex Medical Limited: Sirtex Medical Products Pty Ltd SIR-Spheres (Ytttrium-90 Microspheres); Apr. 1, 2005.
Theragenics Corp.; Therasphere IDOC TM; Aug. 4, 2015.
Tong, A. et al; Yttrium-90 hepatic radioembolization: clinical review and current techniques in interventional radiology and personalized dosimetry; British Journal of Radiology; vol. 89, No. 1062; Jun. 1, 2016.
US FDA; Theresphere IDOC—Humanitarian Device Exemption (HDE); Sep. 14, 2015.
Westcott, M. et al.; The development, commercialization, and clinical context of yttrium-90 radiolabeled resin and glass microspheres; Advances in Radiation Oncology; 2016; vol. 1; pp. 351-364.
Sirtex Medical Limited; SMAC-SIR—Spheres Microspheres Activity Calculator; May 6, 2018.
CN Office Action, dated Apr. 20, 2022 pertaining to CN201980046622.9 filed Jan. 12, 2021.
International Search Report and Written Opinion dated Sep. 24, 2019 pertaining to International Application No. PCT/US2019033011.

\* cited by examiner

CATHETER WITH FLARING TIP

CROSS-REFERENCES TO RELATED APPLICATIONS

This application is a National Stage Entry under 35 U.S.C. § 371 of International Patent Application No. PCT/US2019/032965, entitled "CATHETER WITH FLARING TIP", filed May 17, 2019, which claims the benefit of priority to U.S. Provisional App. No. 62/673,632, entitled "RADIOEMBOLIZATION DELIVERY DEVICE" filed May 18, 2018, the disclosure of which is incorporated by reference herein; and to U.S. Provisional App. No. 62/673,628, entitled "DUAL-STAGE SYRINGES WITH LOCKING MECHANISM" filed May 18, 2018, the disclosure of which is incorporated by reference herein.

TECHNICAL FIELD

The present disclosure relates generally to catheters and, more particularly, to microcatheters configured and operable to deliver a therapeutic agent to an area within a patient's body during transarterial medical procedures.

BACKGROUND

In cancer treatments involving radiation therapy, inadvertent or excess exposure to radiation from radioactive therapeutic agents can be harmful and potentially lethal to patients or medical personnel. Accordingly, medical instruments for radiation therapies must be configured to localize the delivery of radioactive material to a particular area of the patient's body while shielding others from unnecessarily being exposed to radiation.

Transarterial Radioembolization is a transcatheter intra-arterial procedure performed by interventional radiology and is commonly employed for the treatment of malignant tumors. During this medical procedure, a microcatheter is navigated into a patient's liver, where radioembolizing microspheres loaded with a radioactive compound, such as yttrium-90 ($^{90}Y$), are delivered to the targeted tumors. The microspheres embolize blood vessels that supply the tumors while also delivering radiation to kill tumor cells.

Generally, medical devices for performing radioembolization procedures require multiple syringes, external tubing, a vial containing the radioactive compound, and a bulky shield assembly for containing and shielding the radioactive vial. Such devices typically involve time consuming and labor-intensive setup procedures. The complex devices are commonly stationary and thereby limit a physician's mobility in an operating room to within a certain proximity of the device.

SUMMARY

Conventional microcatheters utilized for the delivery of microspheres during embolization treatment methods include a tip that fails to prevent or reduce turbulent flow where the therapeutic agent is expelled from the distal end of such conventional microcatheters.

Accordingly, a need exists for a microcatheter that is configured and operable to perform embolization that incorporates a simplistic design and consistent means for administering constant flow rates and pressure of the therapeutic agent to a vessel in the patient's body.

Embodiments of the present disclosure meet the aforementioned needs by providing a microcatheter with a flaring tip. The flaring tip may prevent reflux and may evenly distribute a therapeutic agent during a medical procedure, such as an embolization procedure.

According to at least one embodiment of the present disclosure, a flaring tip microcatheter is provided. The flaring tip microcatheter may include a hollow shaft having a shaft lumen defined therein, a core disposed within the shaft lumen, and a tip comprising at least two petals affixed to a distal end of the core, the at least two petals comprising at least two wires wherein the core is hollow and defines a core lumen. The at least two wires may be configured to pull the at least two petals to form a flared configuration of the tip. The flared configuration of the tip may allow improved distribution of a therapeutic agent within the vessel. The flared configuration of the tip may allow for laminar flow of a therapeutic agent distally from the tip.

According to at least one embodiment of the present disclosure, a method of deploying a flaring tip microcatheter is provided. The method may include advancing a flaring tip microcatheter having a proximal end and a distal end through a vessel, and pulling the at least two wires to flare the at least two petals and form a flared configuration of the tip, The flaring tip microcatheter may include a hollow shaft having a shaft lumen defined therein, a core disposed within the shaft lumen, and a tip comprising at least two petals affixed to a distal end of the core. The core may be hollow and define a core lumen. The at least two petals may comprise at least two wires. The flared configuration of the tip allows for laminar flow of a therapeutic agent distally from the tip.

According to at least one embodiment of the present disclosure, an embolization treatment method is provided. The method may include advancing a flaring tip microcatheter having a proximal end and a distal end through a vessel within the body of patient, pulling the at least two wires to flare the at least two petals and form a flared configuration of the tip, whereby the flared configuration of the tip allows for laminar flow of a therapeutic agent distally from the tip; and delivering a therapeutic agent to the vessel within the body of the patient comprising expelling the therapeutic agent from the distal end of the flaring tip microcatheter through the core lumen. The flaring tip microcatheter may include a hollow shaft having a shaft lumen defined therein; a core disposed within the shaft lumen, wherein the core is hollow and defines a core lumen; and a tip comprising at least two petals affixed to a distal end of the core, wherein the at least two petals comprise at least two wires. The flared configuration of the tip may allow improved distribution of a therapeutic agent within the vessel.

These and other features, aspects, and advantages of the present disclosure will become better understood with reference to the following description and the appended claims.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Specific embodiments of the present application will now be described. These embodiments are provided so that this disclosure will be thorough and complete and will fully convey the scope of the subject matter to those skilled in the art.

Reference will now be made in detail to embodiments of a flaring tip microcatheter. In embodiments, the flaring tip microcatheter may include three coaxial layers, referred to as a shaft, a core, and a wire layer. In other embodiments, the flaring tip microcatheter may include one or more additional layers. In embodiments, the flaring tip microcatheter may further include a tip, which, by a mechanical method, may be activated or "flared" to produce a flared tip. The flared tip may prevent reflux and may evenly distribute particles delivered within a vessel during a medical procedure. In embodiments, the flared tip of the flaring tip microcatheter may reduce the amount of turbulent flow at the distal end of the flaring tip microcatheter. In further embodiments, the flared tip of the flaring tip microcatheter exhibits less turbulent flow at the distal end of the flaring tip microcatheter compared to the amount of turbulent flow observed at the distal end of conventional catheters. Reducing the amount of turbulent flow at the distal end of the flaring tip microcatheter may allow for improved control over delivery of a therapeutic agent, such as radiotherapeutic microspheres. In other embodiments, reducing the amount of turbulent flow at the distal end of the flaring tip microcatheter may allow for improved control over delivery of embolization product, including scout beads, bland spheres, drug eluting beads, radioembolization spheres, and chemoembolization spheres In other embodiments, the flared tip of the flaring tip microcatheter may be used for flow for occluding a vessel to control flow within the vessel. In further embodiments, the flaring tip microcatheter may block or prevent flow in the vessel.

Figure 1:
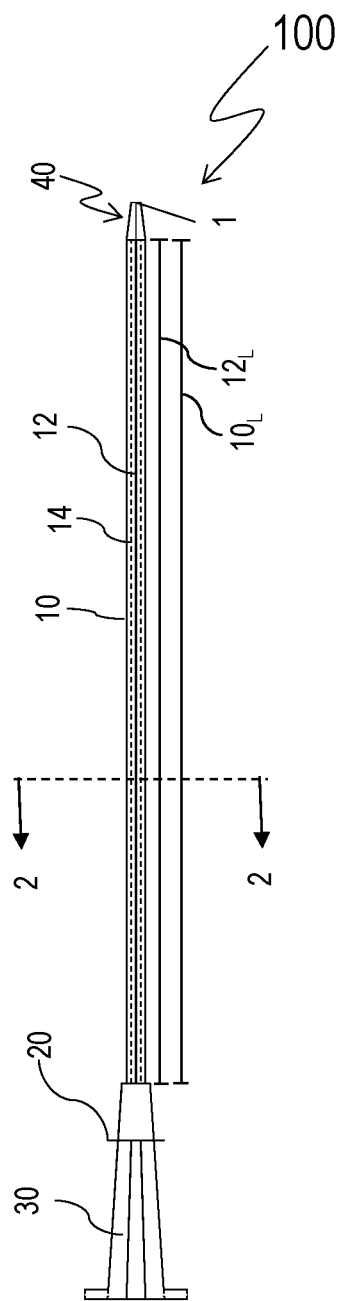
FIG. 1 is an illustration of a cross-section side view of a flaring tip microcatheter in a unflared configuration according to embodiments.

FIG. 1 is a schematic cross-sectional side view of a flaring tip microcatheter in a unflared state in accordance with one embodiment. Referring to FIG. 1, flaring tip microcatheter 100 includes a shaft 10, a core 12, wire layer 14, a slide 20, a hub 30, and a tip 40. Flaring tip microcatheter 100 includes a distal end 1.

As used herein with regard to embodiments of the flaring tip microcatheters, the relative term "distal" means in the direction toward which the distal end 1 of flaring tip microcatheter 100 may be inserted into a vessel and in which a therapeutic agent is expelled from the tip 40 during operation of the flaring tip microcatheter 100. Likewise, the relative term "proximal" means opposite the direction toward which a therapeutic agent is inserted into hub 30 during operation of the flaring tip microcatheter 100. It should be understand in general that directional terms as used herein—for example up, down, right, left, front, back, top, bottom, distal, and proximal—are made only with reference to the figures as drawn and are not intended to imply absolute orientation of any device, of any device component, or of any embodiment as a whole.

Shaft 10 is a hollow tube that defines a lumen through which core 12 extends. Shaft 10 is illustrated as being transparent to allow visualization of features therein. However, in other examples, a shaft similar to shaft 10 is opaque. In embodiments, shaft 10 comprises any biocompatible material such as metals, metal alloys, and polymers. In some embodiments, shaft 10 comprises nylon, Pebax® commercially available from Arkema or any other suitable material known to those of ordinary skill in the art. The shaft 10 may be produced by extrusion methods.

Figure 2:
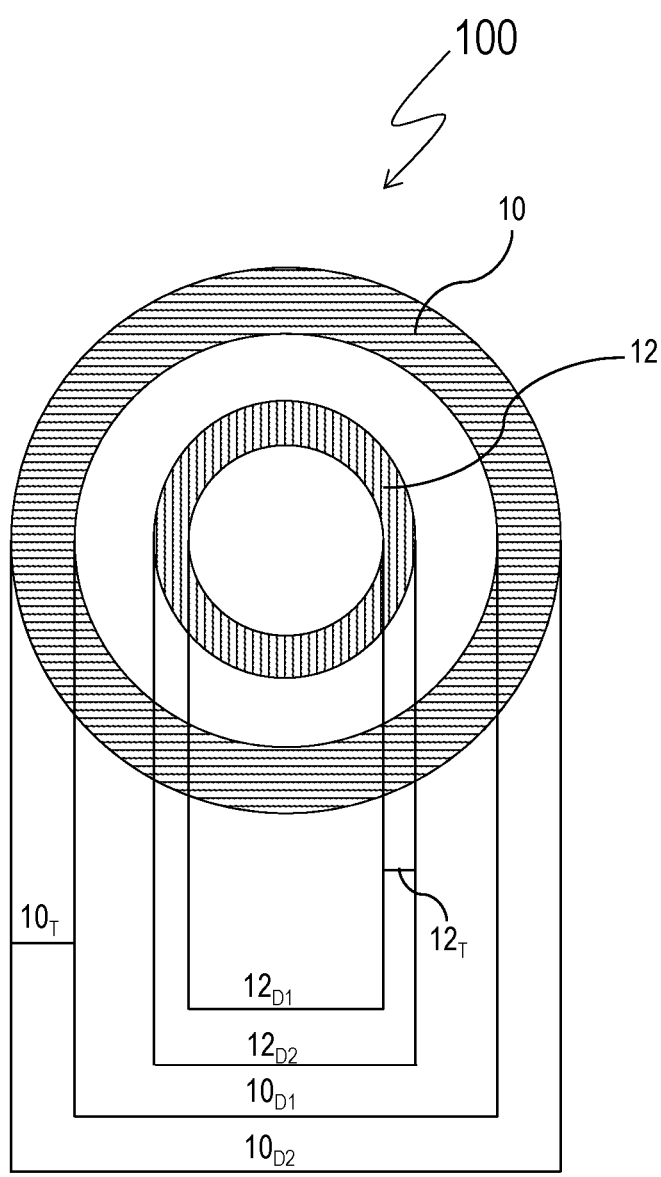
FIG. 2 is an illustration of a cross-section view of the flaring tip microcatheter across line 2-2 of FIG. 1 without showing a wire layer.

Referring again to FIG. 1, shaft 10 may have a shaft length $10_L$, defined as the distance extending from the distal end of the shaft 10 to the proximal end of the shaft 10. As shown in FIG. 2, shaft 10 has a shaft inner diameter $10_{D1}$, an shaft outer diameter $10_{D2}$, and a shaft thickness $10_T$ defined as the distance between the shaft inner diameter $10_{D1}$ and shaft outer diameter $10_{D2}$.

In some embodiments, the shaft length may be from about 100 centimeters (cm) to about 200 cm, from about 100 cm to about 180 cm, from about 100 cm to about 160 cm, from about 100 cm to about 140 cm, from about 100 cm to about 120 cm, from about 120 cm to about 200 cm, from about 120 cm to about 180 cm, from about 120 cm to about 160 cm, from about 120 cm to about 140 cm, from about 140 cm to about 200 cm, from about 140 cm to about 180 cm, from about 140 cm to about 160 cm, from about 160 cm to about 200 cm, from about 160 cm to about 180 cm, or from about 180 cm to about 200 cm.

In some embodiments, the shaft 10 has an shaft inner diameter $10_{D1}$ of from about 0.020 inches (in) (0.508 millimeters (m)) to about 0.030 inches (0.762 mm), from about 0.020 inches to about 0.028 inches, from about 0.020 inches to about 0.026 inches, from about 0.020 inches to about 0.024 inches, from about 0.020 inches to about 0.022 inches, from about 0.022 inches to about 0.030 inches, from about 0.022 inches to about 0.028 inches, from about 0.022 inches to about 0.026 inches, from about 0.022 inches to about 0.024 inches, from about 0.024 inches to about 0.030 inches, from about 0.024 inches to about 0.028 inches, from about 0.024 inches to about 0.026 inches, from about 0.026 inches to about 0.030 inches, from about 0.026 inches to about 0.028 inches, or from about 0.028 inches to about 0.030 inches.

In some embodiments, the shaft outer diameter may be from about 2.0 French (Fr) (0.67 mm) to about 3.0 Fr (1 mm), from about 2.0 Fr to about 2.8 Fr, from about 2.0 Fr to about 2.6 Fr, from about 2.0 Fr to about 2.4 Fr, from about 2.0 Fr to about 2.2 Fr, from about 2.2 Fr to about 3.0 Fr, from about 2.2 Fr to about 2.8 Fr, from about 2.2 Fr to about 2.6 Fr, from about 2.2 Fr to about 2.4 Fr, from about 2.4 Fr to about 3.0 Fr, from about 2.4 Fr to about 2.8 Fr, from about 2.4 Fr to about 2.6 Fr, from about 2.6 Fr to about 3.0 Fr, from about 2.6 Fr to about 2.8 Fr, or from about 2.8 Fr to about 3.0 Fr.

In some embodiments, the shaft thickness may be, for example, 0.009 inches or any thickness that may allow for suitable trackability within the vessel.

Core 12 (illustrated by a solid line in FIG. 1) is a hollow tube and defines a core lumen through which a therapeutic agent may be loaded and expelled. In other embodiments, one or more additional lumens may be incorporated into the shaft 10 of flaring tip microcatheter 100. In some embodiments, the one or more additional lumens which may be specifically configured to accommodate wires, a therapeutic agent, other media, or combinations.

Referring again to core 12, illustrated by a solid line in FIG. 1, in some embodiments, the core-lumen facing surface of the core 12 may be coated, for example with a hydrophilic coating, to allow for improved trackability and improved delivery of a therapeutic agent through the core lumen. In embodiments, core 12 may be made from POLYTETRAFLUOROETHYLENE, ACRYLONITRILE BUTADIENE STYRENE, ACETAL, ARNITEL, BIONATE, CARBOTHANE, CHRONOSIL, EFEP, ELASTOLLAN, ETFE, ETHYL VINYL ACETATE, EVAL, FLUORINATED ETHYLENE PROPYLENE, HIGH DENSITY POLYETHYLENE, HYTREL, KYNAR PVDF, LOW DENSITY POLYETHYLENE, LINEAR LOW DENSITY POLYETHYLENE, MEDALIST, NEOFLON™ EFEP RP-5000, NEOFLON™ PFA AP-210, NYLON 11, NYLON 12, NYLON 6, PEBAX® 35D, PEBAX 45D, PEBAX 55D, PEBAX 63D, PEBAX 70D, PEBAX 72D, PEBAX/EVERGLIDE®, PEBAX/MOBILIZE, PEBAX/PEBASLIDE, PEBAX/PROPELL S™ PEEK, PELLETHANE 55D, PELLETHANE 75D, POLYETHYLENE TEREPHTHALATE, PERFLUOROALKOXY ALKANES, POLYCARBONATE, POLYPROPYLENE, POLYSULFONE, PRIMACOR, POLYVINYL CHLORIDE, RESIN, REZILIENT, SANTOPRENE, SEBS, TECOPLAST, TECOTHANE, TEXIN, THERMOPLASTIC POLYIMIDE, any materials suitable for delivery of the therapeutic agent, and combinations thereof. In some embodiments, the core 12 may be made from a polytetrafluoroethylene. The core 12 may be produced by extrusion methods.

Referring again to FIG. 1, core 12 has a core length $12_L$, defined as the distance extending from the distal end of the core 12 to the proximal end of the core 12. As shown in FIG. 2, core 12 has an core inner diameter $12_{D1}$, an core outer diameter $12_{D2}$, and a core thickness $12_T$ defined as the distance between the core inner diameter $12_{D1}$ and core outer diameter $12_{D2}$. In some embodiments, the core length is from about 100 centimeters (cm) to about 200 cm, from about 100 cm to about 180 cm, from about 100 cm to about 160 cm, from about 100 cm to about 140 cm, from about 100 cm to about 120 cm, from about 120 cm to about 200 cm, from about 120 cm to about 180 cm, from about 120 cm to about 160 cm, from about 120 cm to about 140 cm, from about 140 cm to about 200 cm, from about 140 cm to about 180 cm, from about 140 cm to about 160 cm, from about 160 cm to about 200 cm, from about 160 cm to about 180 cm, or from about 180 cm to about 200 cm. In some embodiments, the core inner diameter $12_{D1}$, the core outer diameter $12_{D2}$, and the core thickness are sized to allow for suitable wire-thread translation. In some embodiments, the core 12 may be concentric with the shaft 10, for example, as illustrated in FIG. 2. In other embodiments, the core 12 extends through the shaft, but the core 12 may not be concentric with the shaft 10.

In embodiments, the flaring tip microcatheter 100 includes a wire layer, which is made up of one or more wires. Referring again to FIG. 1, in embodiments, the wire layer 14 may be disposed between the shaft 10 and the core 12. Between the shaft 10 and the core 12, the wire layer 14 may not interfere with the therapeutic material running through the core 12, be damaged by the therapeutic material (i.e., if the therapeutic material is radiotherapeutic material, which could also limit the materials which may be used for the wires), and may allow for improved or easier pulling of the petals. The proximal end of wire layer 14 may be affixed to the slide 20, and the distal end of wire layer 14 may be affixed to the tip 40. That is, the proximal ends of each wire that makes up the wire layer 14 may be affixed to the slide 20, and the distal ends of each wire that makes up the wire layer 14 may be affixed to the tip 40. In embodiments, the wire may be made of any suitable material, including, but not limited to, nylon, tungsten, stainless steel, and nitinol. In some embodiments, the wires that make up the wire layer 14 may have a coating, for example, a polytetrafluoroethylene coating. The coating on the wires may allow for improved translation of the wires as the wires may be pulled within the flaring tip microcatheter 100. In embodiments, the wires may be of a fixed diameter, may increase in diameter, or may decrease in diameter along the length of the wire.

Figure 3A:
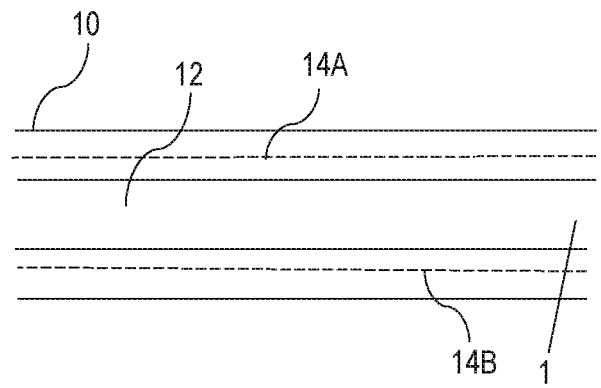
FIG. 3A is an illustration of a partial cross-section side view of a flaring tip microcatheter having two straight wires according to embodiments.
Figure 3B:
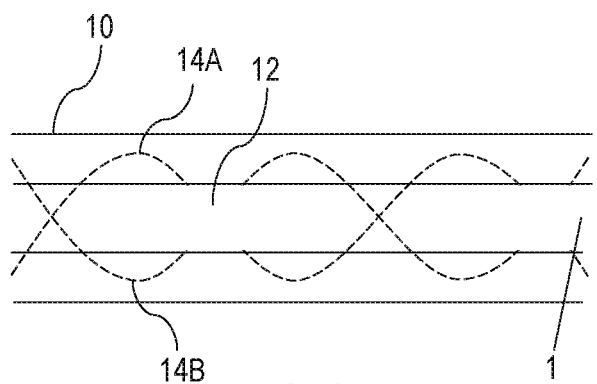
FIG. 3B is an illustration of a partial cross-section side view of a flaring tip microcatheter having two braided wires according to embodiments.
Figure 3C:
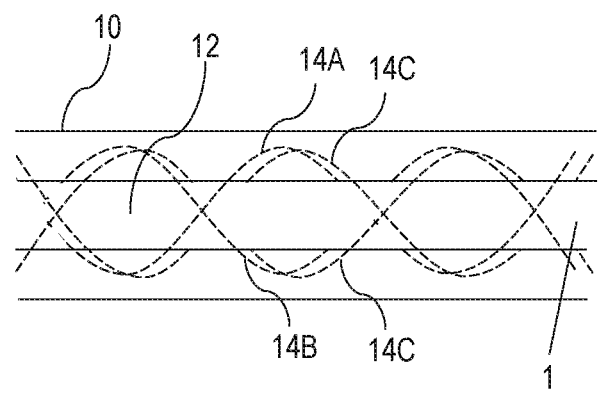
FIG. 3C is an illustration of a partial cross-section side view of a flaring tip microcatheter having four braided wires according to embodiments.

Referring now to FIGS. 3A, 3B, and 3C, wire layer 14 is represented by one or more dotted lines in each figure respectively. In each of FIGS. 3A, 3B, and 3C, each dotted line represents an individual wire. Therefore, wire layer 14 is comprised of one or more wires. In FIG. 3A, wire layer 14 includes wire 14A and wire 14B. In the embodiment shown in FIG. 3A, wire 14A and wire 14B extend in a straight line along the same horizontal (longitudinal) axis as the core 12 and the shaft 10. In other embodiments, only one wire or more than two wires may compose the wire layer 14 and extend in a straight line along the same horizontal axis as the core 12 and the shaft 10. Referring now to FIG. 3B, the wire layer 14 includes two wires as in the embodiment of FIG. 3A, wire 14A and wire 14B. In FIG. 3B, wire 14A and wire 14B intertwine in a braided manner around the core 12 extending along the same horizontal axis as the core 12 and the shaft 10. Referring now to FIG. 3C, the wire layer 14 now includes four wires, wire 14A, wire 14B, wire 14C, and wire 14D, which each intertwine in a braided manner around the core 12 extending along the same horizontal axis as the core 12 and the shaft 10. In other embodiments, only one wire or more than two or four wires may make up the wire layer 14 and intertwine in a braided manner around the core 12 extending along the same horizontal axis as the core 12 and the shaft 10. In embodiments where the wires are intertwined in a braided manner around the core 12, how tightly the wires are intertwined may vary. In other embodiments not shown in FIGS. 3A-C, the wires may be intertwined twisted or otherwise wrapped around core 12 in a manner that is not braided. In embodiments, running the wires straight through the wire layer 14 may allow for a more simplistic design of the flaring tip microcatheter 100, which may be beneficial for design or manufacturing purposes. For example, running the wires straight through the wire layer 14 may allow for easier facilitation of the movement of the wires. In other embodiments, twisting or braiding the wires may reinforce and/or strengthen wire layer 14 and/or provide improved flexibility, pushability and directability of wire layer 14.

In embodiments, the flaring tip microcatheter 100 includes a tip 40. In some embodiments, the tip 40 may comprise one or more coverings and/or visualization markers to aid in locating and positioning the stent within a vessel. For example, the tip 40 may comprise a radiopaque marker and/or coating made of one or more of gold, platinum, tantalum, etc. that may be indirectly visualized. The tip 40 may include one or more petals and a portion of the individual wires of the wire layer 14 that are affixed to the petals. The proximal end of tip 40 may be affixed to or mounted on the distal end of core 12 within the lumen of the shaft 10. More specifically, in embodiments, the petals of the tip 40 may be disposed between the core 12 and the shaft 10, where the petals are affixed to the core 12. In further embodiments, the petals may be wrapped around core 12. In embodiments, the petals may be POLYTETRAFLUOROETHYLENE, ACRYLONITRILE BUTADIENE STYRENE, ACETAL, ARNITEL, BIONATE, CARBOTHANE, CHRONOSIL, EFEP, ELASTOLLAN, ETFE, ETHYL VINYL ACETATE, EVAL, FLUORINATED ETHYLENE PROPYLENE, HIGH DENSITY POLYETHYLENE, HYTREL, KYNAR PVDF, LOW DENSITY POLYETHYLENE, LINEAR LOW DENSITY POLYETHYLENE, MEDALIST, NEOFLON™ EFEP RP-5000, NEOFLON™ PFA AP-210, NYLON 11, NYLON 12, NYLON 6, PEBAX® 35D, PEBAX 45D, PEBAX 55D, PEBAX 63D, PEBAX 70D PEBAX 72D PEBAX/EVERGLIDE®, PEBAX/MOBILIZE PEBAX/PEBASLIDE, PEBAX/PROPELL S™ PEEK, PELLETHANE 55D, PELLETHANE 75D, POLYETHYLENE TEREPHTHALATE, PERFLUOROALKOXY ALKANES, POLYCARBONATE, POLYPROPYLENE, POLYSULFONE, PRIMACOR, POLYVINYL CHLORIDE, RESIN, REZILIENT, SANTOPRENE, SEBS, TECOPLAST, TECOTHANE, TEXIN, THERMOPLASTIC POLYIMIDE, NITINOL, STAINLESS STEEL, POLYMER, any suitable flexible material, or other resilient material.

In embodiments, tip 40 includes a plurality of petals, collectively referred to as petals 46. Referring now to FIGS. 4-8 together, embodiments, the tip 40 may have a distal opening 48 formed at the distal end 4 of tip 40. In embodiments, the petals 46 may include any number of petals and any number of rows of petals suitable for preventing reflux and evenly distributing particles delivered within a vessel during a medical procedure. In some embodiments, the petals 46 may be suitable for occluding a vessel to control flow within the vessel. In further embodiments, the petals 46 may block or prevent flow in the vessel.

Figure 4:
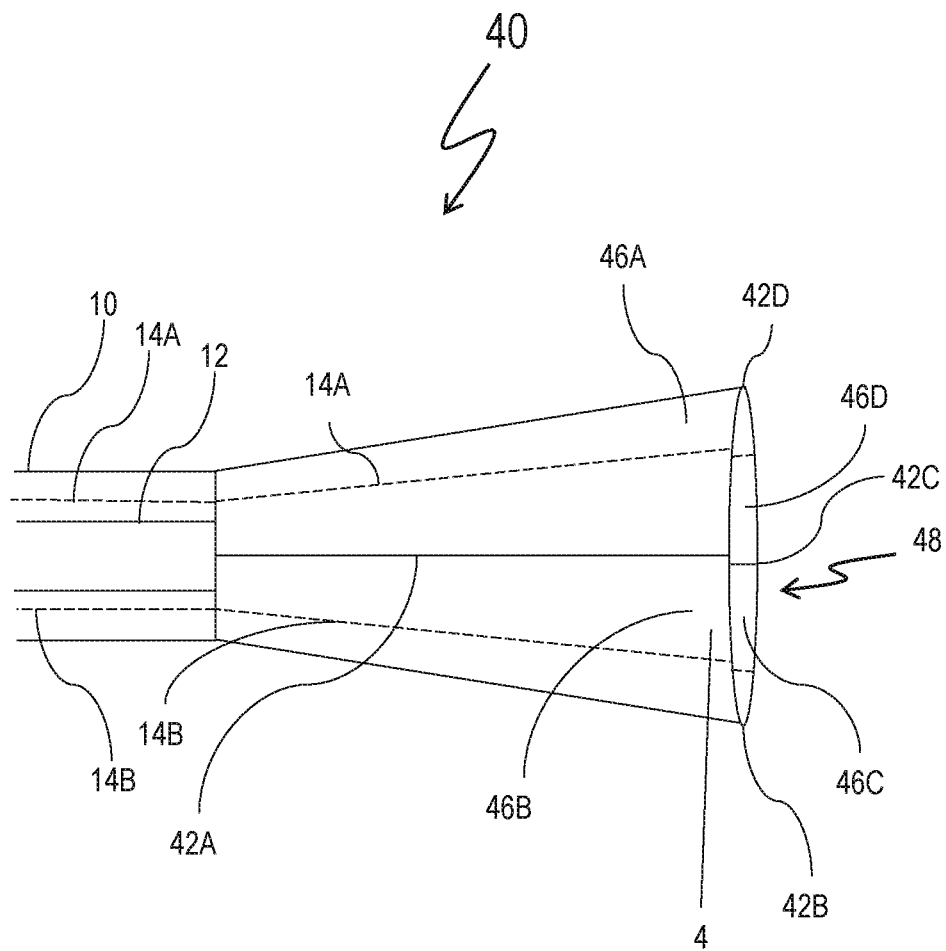
FIG. 4 is an illustration of a side view of the tip of a flaring tip microcatheter having four petals according to embodiments.

In accordance with the embodiment illustrated by FIG. 4, tip 40 includes four petals 46A, 46B, 46C, 46D, although tip 40 may have more or fewer petals in other embodiments. Illustratively, petal 46A, petal 46B, petal 46C, and petal 46D are elongate, flat members having a squared-off distal end. In FIG. 4, the proximal end of tip 40 is affixed to the distal end of core 12 and the distal end of shaft 10. In the embodiment illustrated in FIG. 4, wire 14A and wire 14B are affixed to petal 46A and petal 46B, respectively. In some embodiments, a wire may be affixed to the external surface of a petal, which is the surface of the petal opposite the surface through which the therapeutic agent may be expelled from the tip 40. In other embodiments, the wire may be incorporated within the petal. In some embodiments, the wire may be affixed in the center of the petal, but in other embodiments, the wire may be affixed off-center in or on the petal, or multiple wires may be affixed to the petal. For example, in some embodiments, a first wire may be affixed to a right region of the external surface of the petal, and a second wire may be affixed to a left region of the external surface of the petal. Referring again to FIG. 4, between petal 46A and petal 46B is a seam 42A. In other embodiments, at seam 42A, petal 46A and petal 46B may meet but not overlap. In FIG. 4, petal 46A, which includes wire 14A, meets petal 46B, which includes wire 14B at seam 42A; petal 46B, meets petal 46C, which includes wire 14C at seam 42B; petal 46C, meets petal 46D, which includes wire 14D at seam 42C; and petal 46D, meets petal 46A, at seam 42D. At any of the individual seams 42A, 42B, 42C, 42D, collectively referred to as seams 42, the two petals that meet at each seam may overlap. In other embodiments, the two petals that meet at each seam may not overlap. For example, at seam 42A, petal 46A and petal 46B may meet and overlap or not overlap. When two or more petals overlap at a seam, the overlapping may reduce the amount of turbulent flow at the distal end of the flaring tip microcatheter.

Figure 5:
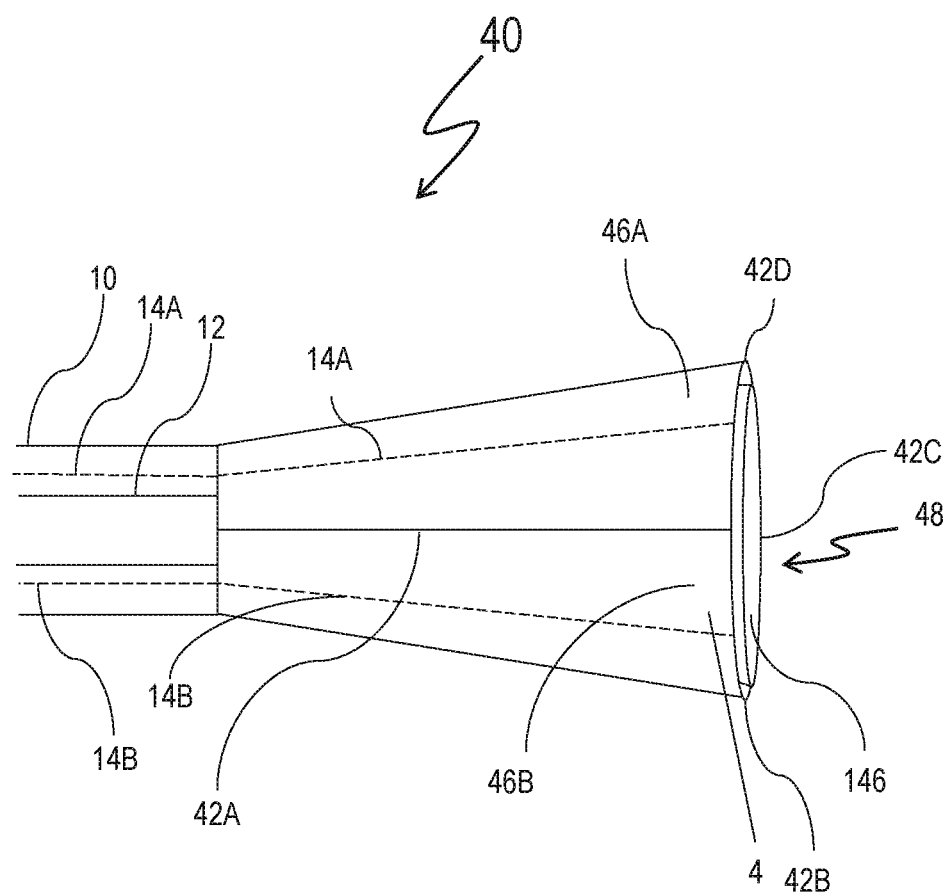
FIG. 5 is an illustration of a side view of the tip of a flaring tip microcatheter having four petals and an additional row of petals according to embodiments.

The embodiment of the tip 40 in FIG. 5 is similar to the embodiment of FIG. 4 and further includes a second row of petals 146. Although, for simplicity, petals 146 are represented as a single member in FIG. 5, embodiments of flaring tip microcatheter 100 may include one or more rows of petals, where each row may include one or more petals. In some embodiments that include two or more rows of petals, more than two petals may meet at each seam. In some embodiments one or more additional rows of petals may further reduced reflux or increase distribution of a therapeutic agent.

Figure 6:
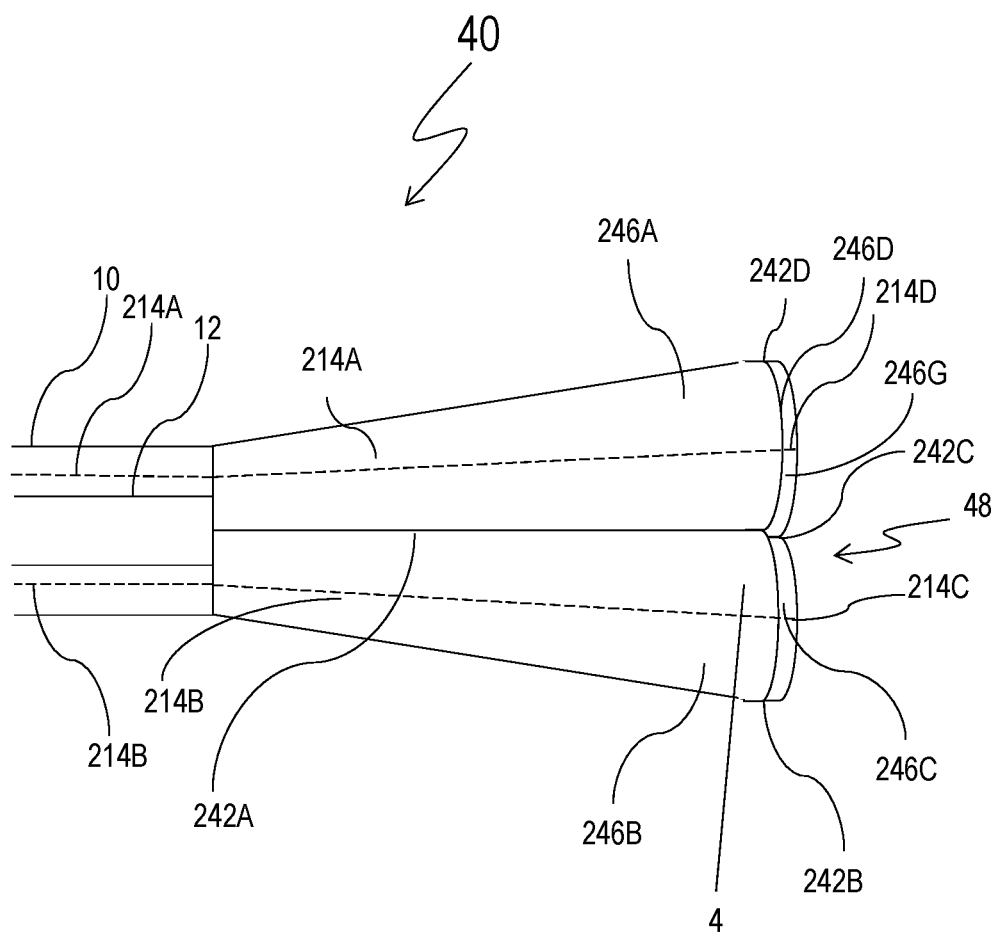
FIG. 6 is an illustration of a side view of the tip of a flaring tip microcatheter having four petals according to embodiments.

Referring now to the embodiment of the tip 40 in FIG. 6, tip 40 includes four petals, 246A, 246B, 246C, 246D, which are elongate, flat members having a rounded distal end. In FIG. 6, petal 246A, which includes wire 214A, meets petal 246B, which includes wire 214B at seam 242A; petal 246B, meets petal 246C, which includes wire 214C at seam 242B; petal 246C, meets petal 246D, which includes wire 214D at seam 242C; and petal 246D, meets petal 246A, at seam 242D.

Figure 7:
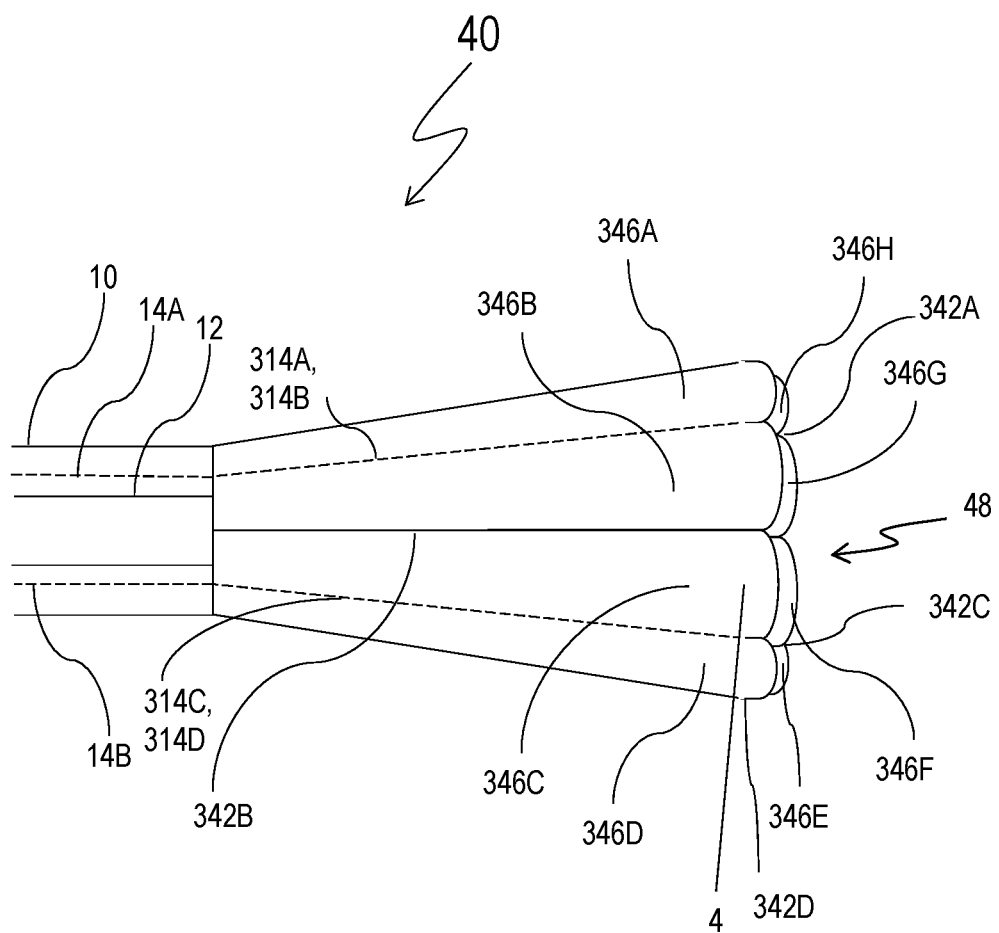
FIG. 7 is an illustration of a side view of the tip of a flaring tip microcatheter having four petals according to embodiments.

In FIG. 7, tip 40 again includes four petals, 346A, 346B, 346C, 346D, which are elongate, flat members that are tapered in the center, along with an additional four petals 346E, 346F, 346G, 346H. In FIG. 7, petal 346A, which includes wire 314A, meets petal 346B, which includes wire 314B at seam 342A; petal 346B, meets petal 346C, which includes wire 314C at seam 342B; petal 346C, meets petal 346D, which includes wire 314D at seam 342C; and petal 346D, meets petal 346A, at seam 342D. In addition to the embodiments represented by FIGS. 4, 6, and 7 the distal ends of petals 46 may be of any shape suitable for preventing reflux and for evenly distributing particles delivered within a vessel during a medical procedure.

Figure 8:
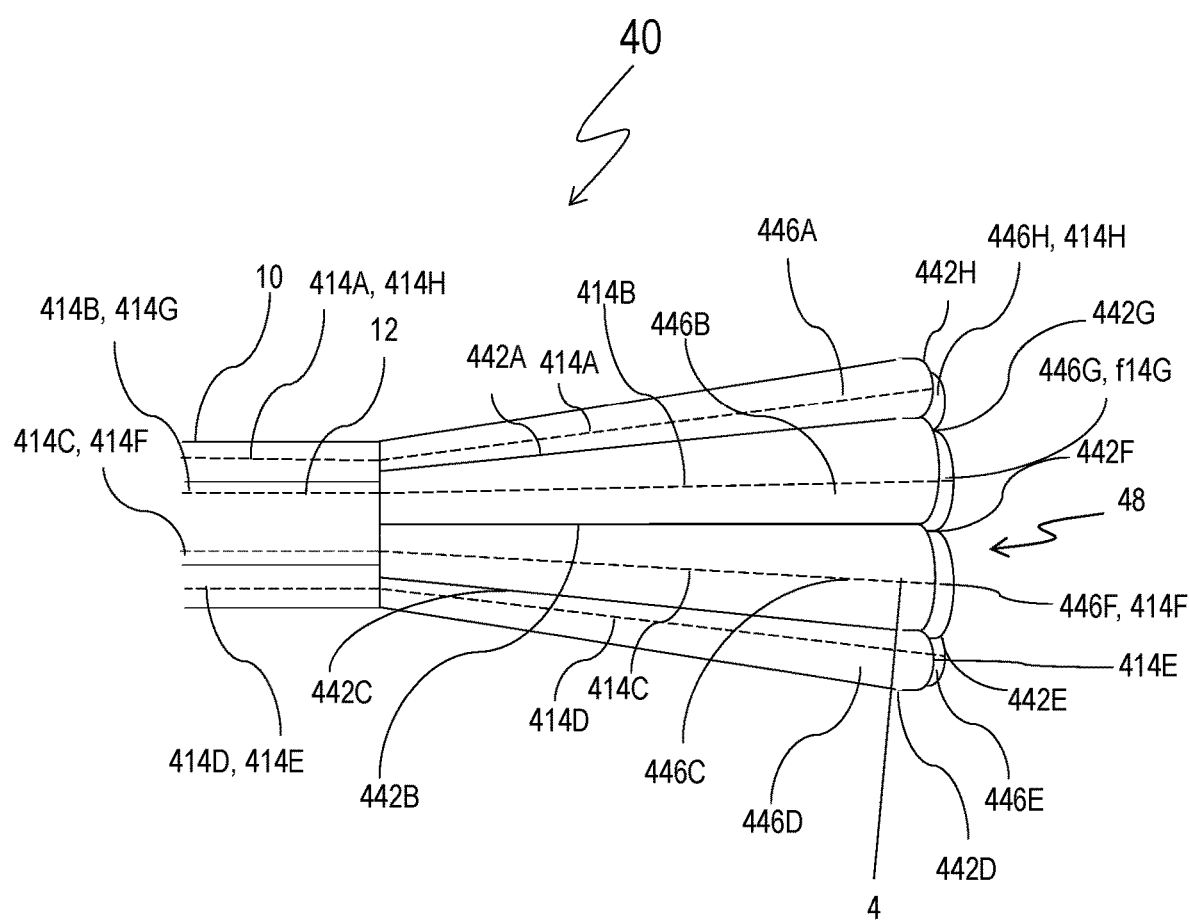
FIG. 8 is an illustration of a side view of the tip of a flaring tip microcatheter having eight petals according to embodiments.

Referring now to the embodiment of the tip 40 in FIG. 8, tip 40 includes eight petals, 446A, 446B, 446C, 446D, 446E, 446F, 446G, 446H, which are elongate, flat members having a rounded distal end. In some embodiments, increasing the number of petals may further reduced reflux or increase distribution of a therapeutic agent. As stated previously, tip 40 may have more or less petals in other embodiments. In FIG. 8, petal 446A, which includes wire 414A, meets petal 446B, which includes wire 414B at seam 442A; petal 446B, meets petal 446C, which includes wire 414C at seam 442B; petal 446C, meets petal 446D, which includes wire 414D at seam 442C; petal 446D, meets petal 446E, which includes wire 414E at seam 442D; petal 446E, meets petal 446F, which includes wire 414F at seam 442E; petal 446F, meets petal 446G, which includes wire 414G at seam 442F; petal 446G, meets petal 446H, which includes wire 414H at seam 442G; and petal 446H, meets petal 446A, at seam 442H.

Figure 9A:
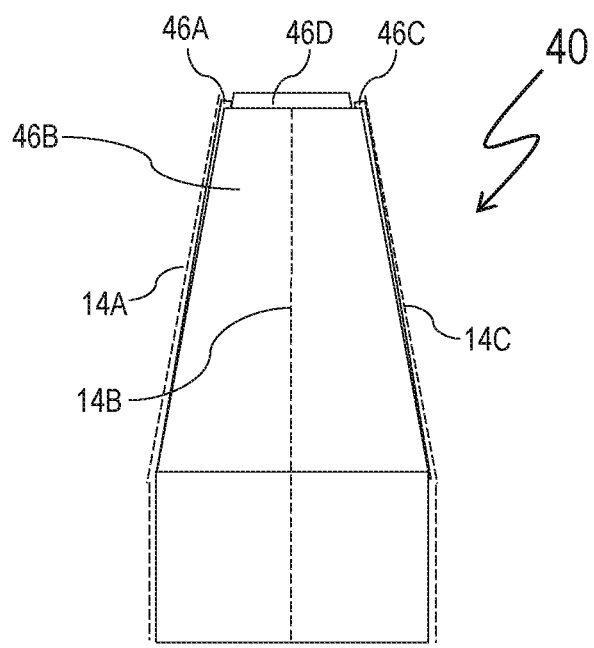
FIG. 9A is an illustration a side view of the tip of a flaring tip microcatheter in an unflared configuration according to embodiments.
Figure 9B:
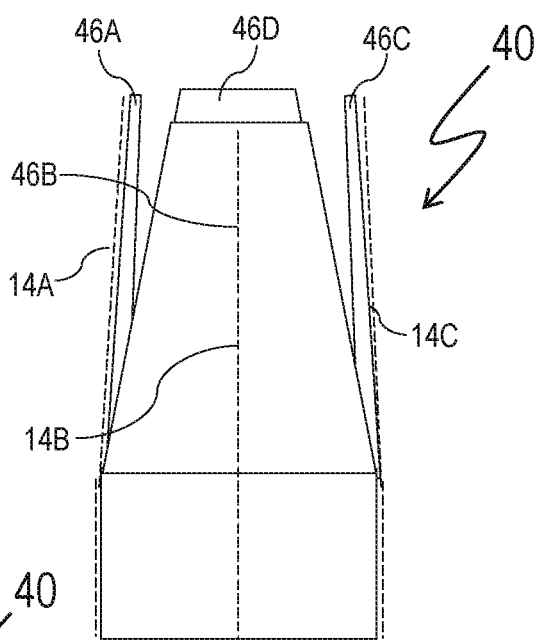
FIG. 9B is an illustration of a side view of the tip of a flaring tip microcatheter in a transition configuration according to embodiments.
Figure 9C:
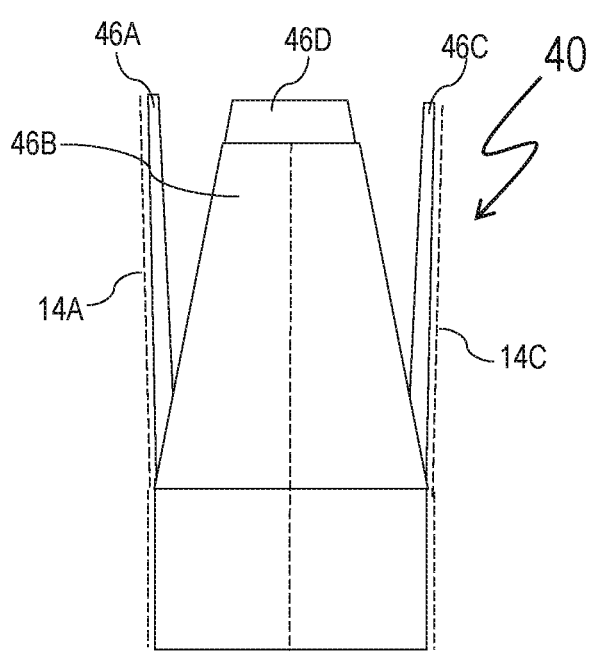
FIG. 9C is an illustration of a side view of the tip of a flaring tip microcatheter in an flared configuration according to embodiments.

FIGS. 9A-9C illustrate how the wires affixed to each petal of tip 40 may pull back the petals 46 or otherwise move the petals 46 in a proximal direction, thereby radially expanding the petals outward from one another or "flaring" the tip 40. FIG. 9A shows flaring tip microcatheter 100 in the unflared configuration. In FIG. 9B showing flaring tip microcatheter 100 in a transition configuration, wire 14A, wire 14B, wire 14C, and wire 14D (not shown in FIG. 3B) have begun to pull back on petal 46A, petal 46B, petal 46C, and petal 46D, respectively. FIG. 9C then shows flaring tip microcatheter 100 in the flared configuration, where wire 14A, wire 14B, wire 14C, and wire 14D (not shown in FIG. 3C) have fully pulled back on petal 46A, petal 46B, petal 46C, and petal 46D, respectively. In other embodiments, the petals 46 may be pulled back to a greater or lesser extent than illustrated in FIG. 9C. In embodiments, the wires of the wire layer 14 may pull back the petals 46 of the tip 40, or otherwise move the petals 46 in a proximal direction, to an extent that prevents reflux and evenly distributes particles delivered from tip 40 to a vessel during a medical procedure. In some embodiments, the petals 46 may be suitable for occluding a vessel to control flow within the vessel. In further embodiments, the petals 46 may block or prevent flow in the vessel.

Figure 10A:
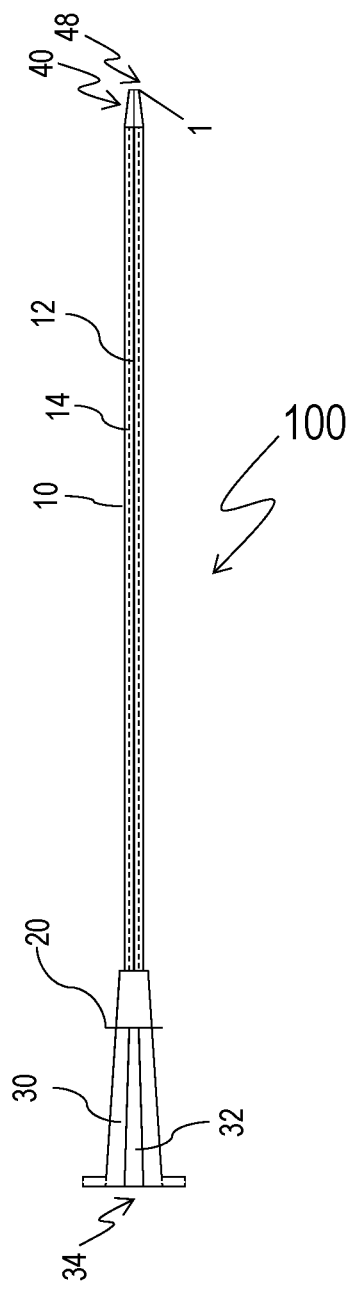
FIG. 10A is an illustration of a flaring tip microcatheter in an unflared configuration according to embodiments.

Referring now to FIG. 10A, an illustration of a flaring tip microcatheter 100 in a unflared configuration according to embodiments is provided. In FIG. 10A, petals including wires collectively form the tip 40. In its unflared configuration illustrated in FIG. 10A, the petals of tip 40 form a conical shape that gradually decreases in diameter towards the distal end of flaring tip microcatheter 100. In the unflared configuration, the petals of tip 40 are substantially in contact with one another along the entire length of the petals. The shape of tip 40 in the unflared configuration may provide improved trackability in vessels during a medical procedure. As stated previously, tip 40 includes distal opening 48 therein allowing passage of a guidewire (not shown) through tip 40.

Figure 10B:
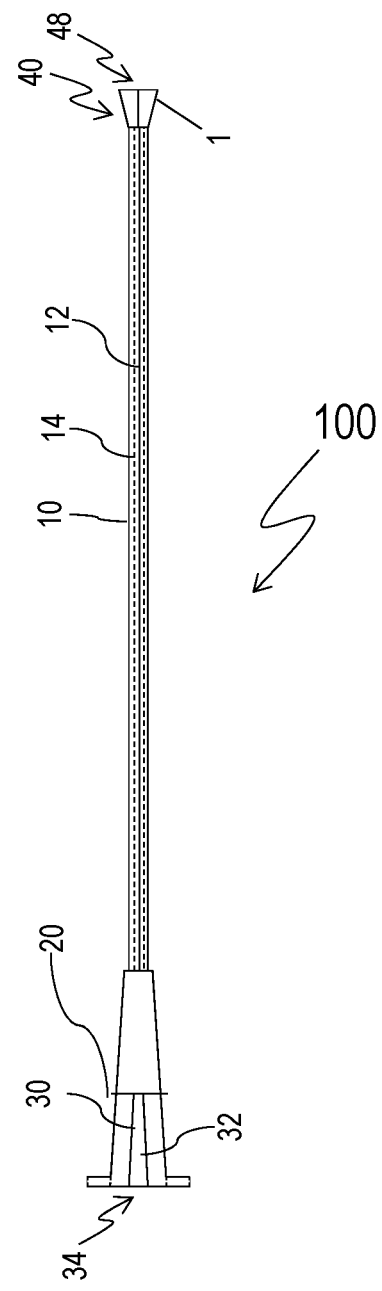
FIG. 10B is an illustration of a flaring tip microcatheter in a flared configuration according to embodiments.

Referring now to FIG. 10B, an illustration of a flaring tip microcatheter 100 in a flared configuration according to embodiments is provided. In FIG. 10B, in the flared configuration of flaring tip microcatheter 100, a slide 20 has been advanced towards the proximal end of flaring tip microcatheter 100. The wires of the wire layer 14 are connected to slide 20 in a manner that allows slide 20 to proximally advance, or slide, pulling the wires of wire layer 14, thereby opening the petals of tip 40, which results in the flared configuration. In embodiments, the flaring tip microcatheter 100 may arrive at the flared configuration when the slide 20 can no longer be advanced towards the proximal end of flaring tip microcatheter 100. In some embodiments, slide 20 may include one or more teeth (not pictured) adapted to ratchet the slide 20 at various incremental stopping points as the slide 20 advances towards the proximal end of flaring tip microcatheter 100. At these various stopping points, the petals are radially expanded incrementally.

Embodiments of flaring tip microcatheter 100 may include a hub 30. Hub 30 may be affixed to the proximal end of shaft 10. Referring to FIGS. 10A and 10B, hub 30 comprises a hub lumen 32. In embodiments, a guidewire, one or more therapeutic agents, or both may pass through the hub lumen 32. In some embodiments, a guidewire, one or more therapeutic agents, or both may enter the hub lumen 32 at a proximal opening 34. The guidewire, the one or more therapeutic agents, or both may then pass through the hub lumen 32 towards the distal end 1 of flaring tip microcatheter 100, through the core lumen, through the tip 40, and subsequently be expelled out of the distal opening 48. In embodiments, hub 30 comprises any biocompatible material such as metals, metal alloys, and polymers. In some embodiments, hub 30 comprises nylon, Pebax®, or any other suitable material known to those of ordinary skill in the art.

In embodiments, the hub 30 may include a strain relief system. In some embodiments, the strain relief system may attach individual wires of the wire layer 14 to a spring or coil. In further embodiments, the proximal end of individual wires of the wire layer 14 may be attached to a spring or coil. When the spring is in a compressed state, the petals of the tip 40 may be closed so that the flaring tip microcatheter 100 is in an unflared configuration. As the slide 20 may be proximally advanced, or slid, pulling the wires of wire layer 14, the spring stretches and pulls the petals of the tip 40. The strain relief system may provide tension that allows the wires and/or petals to be pulled without undue stress on the flaring tip microcatheter 100.

In some variations, the flaring tip microcatheter 100 may comprise a visual detection portion for indirectly visualizing the location and/or orientation of the flaring tip microcatheter 100. The visual detection portion may be visualized using a technique such as fluoroscopy during deployment of the flaring tip microcatheter 100. In some instances, one or more characteristics of the flaring tip microcatheter 100 such as echogenicity, radiopacity, surface area, surface area, permittivity, conductivity, permeability, and the like may be selected to enhance detection by, for example, fluoroscopy and/or a detector. Fluoroscopy is a technique for real-time X-ray imaging where, generally, an X-ray beam is emitted from a fluoroscope through an area of interest in a body. Objects to be visualized (e.g., stents) may be imaged using an image intensifier. A user viewing the real-time images shown by the image intensifier may then determine the location and orientation of the flaring tip microcatheter 100 and use it to guide flaring tip microcatheter 100 deployment.

Reference will now be made to embodiments of methods of deploying a flaring tip microcatheter. In embodiments, the methods of deploying a flaring tip microcatheter may include providing a flaring tip microcatheter according to embodiments described herein. Then, in some embodiments, a guidewire may be guided through a vessel within a body. In some embodiments, the flaring tip microcatheter 100 may be advanced over the guidewire and guided through a vessel within a body. In other embodiments, the flaring tip microcatheter 100 may be advanced through a vessel within a body without a guidewire. Once the flaring tip microcatheter 100 reaches a treatment site within the vessel, the method may further include pulling the wires of wire layer 14 to radially expand the petals 46 outward from one another and "flare" the tip 40, thereby forming a flared configuration of the flaring tip microcatheter 100. In the flared configuration of flaring tip microcatheter 100, a therapeutic agent may be deployed and flow distally from the tip 40 out of the distal opening 48 in a laminar manner.

After deployment of a therapeutic agent, such as a radiotherapeutic agent, a chemotherapeutic agent, or combinations thereof, slide 20 may be moved towards the distal end of flaring tip microcatheter 100, thereby collapsing the tip 40 back to the unflared configuration, and flaring tip microcatheter 100 may subsequently be removed from the patient.

Reference will now be made to embodiments of producing a flaring tip microcatheter. In embodiments, to produce a flaring tip microcatheter, a core 12 may be extruded and cut to length. The core 12 may be extruded using any suitable material, such as polytetrafluoroethylene. In further embodiments, a shaft 10 may be extruded and cut to length. The shaft 10 may be extruded using any suitable material, such as Pebax® commercially available from Arkema. The shaft 10 may extruded having a greater shaft inner diameter than the core outer diameter of the core 12.

Once the core 12 and the shaft 10 have been produced, two or more wires may be extended straight along, twisted along, braided along, or otherwise extended along the length of the core 12 forming a wire layer 14. Then, the shaft 10 may be slid over the wire layer 14 and the core 12. In other embodiments, once the core 12 and the shaft 10 have been produced, two or more wires may be inserted or threaded between the shaft 10 and the core 12 and extended straight through, twisted through, braided through, or otherwise extended through the shaft lumen along the length of the core 12 forming a wire layer 14. Once the wire layer 14 has been formed, the shaft 10 and the core 12 may be fused together using heat to entrap the wire layer 14 between the shaft 10 and the core 12.

In embodiments, the length of the wires in the wire layer 14 may extend beyond the distal end of the shaft 10 and the distal end of the core 12. In further embodiments, the length of the wires in the wire layer 14 may be flush with the proximal end of the shaft 10 and the proximal end of the core 12.

Then, in embodiments, the distal end of the core 12 and the shaft 10 may form an uncut tip by any suitable method such as radio frequency (RF) tipping methods or hot dye methods known in the art. Once formed and cooled, the uncut tip would be cut into individual petals using a cutting dye, thereby forming the tip 40.

The proximal end of the shaft 10 may be molded to form the hub 30 or may be bonded to the hub 30 by any suitable means, such as using an adhesive. For example the proximal end of the shaft 10 may be bonded to the hub 30 using an UV-curable glue. In some embodiments, the hub 30 may include a strain relief.

In embodiments, a slide 20 may be overmolded onto the hub 30. The proximal ends of the individual wires of the wire layer 14 may be pulled taut and/or welded or adhered to the slide 20 that was over molded on the hub. In embodiments, the strain relief may be adhered onto the slide 20, thereby encasing the exposed wires.

Reference will now be made to therapeutic agents and microspheres comprising therapeutic agents, any of which may be delivered with the flaring tip microcatheters according to embodiments described herein or used as the therapeutic agent in methods for deploying a flaring tip microcatheter according to embodiments described herein, or used as the therapeutic agent in embolization treatment methods including the flaring tip microcatheter according to embodiments described herein.

The microspheres or "plurality of microspheres" may include multiple microspheres, which may alternatively be referred to as a "microbeads." In embodiments, the plurality of microspheres includes a therapeutic agent. In further embodiments, the plurality of microspheres may include microspheres that comprise a diamagnetic material, a therapeutic agent, a microbead material, or combinations thereof. In some embodiments, each microbead in the plurality of microspheres may include the diamagnetic material, the therapeutic agent, and the microbead material. In some embodiments, only some of the microspheres in the plurality of microspheres may include the diamagnetic material, the therapeutic agent, or a combination of the diamagnetic material and the therapeutic agent.

Individual microspheres of the plurality of microspheres may have diameters of a size suitable radioembolization medical treatment. In some embodiments, individual microspheres of the plurality of microspheres may have diameters of about 30 micrometers (μm) to about 1500 μm. In other embodiments, the individual microspheres of the plurality of microspheres may have diameters of about 30 μm to about 1500 μm, about 30 μm to about 1000 μm, about 30 μm to about 500 μm, about 30 μm to about 100 μm, about 100 μm to about 1500 μm, about 100 μm to about 1000 μm, about 100 μm to about 500 μm, about 500 μm to about 1500 μm, about 500 μm to about 1000 μm, or about 1000 μm to about 1500 μm.

The microspheres of the plurality of microspheres may include a microbead material. In some embodiments, the microbead material may include glass or silica. In other embodiments, the microbead material may include biodegradable and bioresorbable materials, which are materials that degrade and/or are reabsorbed safely within the body. Examples of biodegradable and bioresorbable materials may include, without limitation, polyglycolic acid (PGA), polyhydroxy butyrate (PHB), polyhydroxy butyrates-co-beta hydroxyl valerate (PHBV), polycaprolactone (PCL), Nylon-2-nylon-6, polylactic-polyglycolic acid copolymers, PLGA-polyethylene glycol (PEG)-PLGA (PLGA-PEG-PLGA), carboxymethylcellulose-chitosan (CMC-CCN), chitosan, hydroxyethyl acrylate (HEA), iron-based alloys, magnesium-based alloys, and combinations thereof. In other embodiments, the microbead material may be a polymer material. In further embodiments, the microbead material may be a water-swellable polymer material, such as a polymer material capable of forming a hydrogel. The microspheres of the plurality of microspheres may have any shape common to microparticles formed from microbead material, or more specifically, a hydrogel type water-swellable polymer material. For example, the microspheres of the plurality of microspheres may be spherical or substantially spherical, may have an ovoid shape with oval-shaped or elliptical cross-sections about a longitudinal axis and circular cross-sections about an axis perpendicular to the longitudinal axis, or combinations thereof. In some embodiments, the microspheres may be porous.

In various embodiments, the microbead material may include water-swellable polymer material that includes a natural hydrogel polymer such as a chitosan or a polysaccharide, or a synthetic hydrogel polymer such as a poly-acrylate, a polyamide, a polyester, a polysaccharide, a poly(methylmethacrylate), or a poly(vinyl alcohol), for example. In some embodiments, the water-swellable polymer material may be biodegradable. Specific examples of water-swellable polymer materials include, without limitation, poly(4-hydroxybutyrate), methacrylated hyaluronic acids (hyaluronic acids being polymers of disaccharides composed of D-glucuronic acid and N-acetyl-D-glucosamine), chitosan-alginates, poly(N-isopropylacrylamide) copolymers, poly(N-isopropylacrylamide)-alginates, poly(N-isopropylacrylamide)-peptides, poly(N-isopropylacrylamide)-α-acryloyloxy-β,β-dimethyl-γ-butyrolactone-hydrophilic Jeffamine, or poly(N-isopropylacrylamide)-poly(ethylene glycol) diacrylate-pentaerythritol tetrakis(3-mercapto-propionate). The microbead material may include may include water-swellable polymer materials that include derivatives of any of the foregoing materials, or may include combinations of any of the foregoing materials or their derivatives. For example, the microbead material may include a combination of multiple water-swellable polymer materials, in which each individual microbead is made of a single type of polymer, and the plurality of microspheres includes microbead materials of multiple polymer types. In some embodiments, the microbead material may include a combination of multiple water-swellable polymer materials, in which individual microspheres are composed of multiple types of polymer.

In embodiments, the individual microspheres of the plurality of microspheres may include from about 30% by weight to about 70% by weight, or from about 35% by weight to about 65% by weight, or from about 40% to about 60% by weight, or about 45% by weight to about 55% by weight, or about 50% to about 70% by weight microbead material, based on the total weight of the individual microspheres. In further embodiments, individual microspheres of the plurality of microspheres may include from about 30% by weight to about 70% by weight, or from about 35% by weight to about 65% by weight, or from about 40% to about 60% by weight, or about 45% by weight to about 55% by weight, or about 50% to about 70% by weight water-swellable polymer material, based on the total weight of the individual microspheres in the plurality of microspheres.

In embodiments, the plurality of microspheres may include one or more diamagnetic materials, which may exhibit magnetic repulsion to an external magnetic field thereby allowing the plurality of microspheres to move according to the magnetic repulsion. In some embodiments, the one or more diamagnetic materials of the plurality of microspheres may exhibit electromagnetic repulsion to an applied electrical current, an electrical field, or both, which thereby allows the plurality of microspheres to move according to the electromagnetic repulsion.

Illustrative materials that react to an electrical current or electrical field may include, but are not limited to, metals, electrolytes, superconductors, semiconductors, nonmetallic conductors, conductive polymers, shape memory polymers, and shape memory alloys. In embodiments, illustrative diamagnetic materials may include, but are not limited to, water, wood; glass; ceramics; graphite; organic compounds such as petroleum, plastic, biological tissue; and metals such as copper, mercury, gold, and bismuth. In some embodiments, the one or more microspheres may include one or more of glass, ceramics, graphite, metals, or combinations thereof. In some specific embodiments, the one or more microspheres may include one or more of graphite, bismuth, or combinations thereof.

In the microspheres of the plurality of microspheres, the one or more diamagnetic materials may be generally surrounded by the microbead material. In some embodiments, the water-swellable polymer material or some portion thereof may generally surround the one or more diamagnetic materials. In other embodiments, a microbead material shell, such as a water-soluble polymer material shell, may encapsulate a core that holds the one or more diamagnetic materials. In other embodiments, the one or more diamagnetic materials may be physically disposed within a matrix, network, or pore structure of the microbead material that may or may not have a core within an outer shell. In other embodiments, the one or more diamagnetic materials may be coated onto or otherwise chemically-bonded to the microbead material, such that the one or more diamagnetic materials have covalent chemical bonds with the microbead material.

In embodiments, the one or more diamagnetic materials may lack covalent chemical bonds with the microbead material but may in some instances interact noncovalently, ionically, or through van der Waals forces with the microbead material. For example, if the microbead material is a polymer material, the one or more diamagnetic materials may lack covalent bounds with the polymer material entirely or the microbead material may lack covalent bonds with just the polymer backbone of the polymer material. In further embodiments, the one or more diamagnetic materials may lack covalent bonds with the water-swellable polymer material entirely or the microbead material may lack covalent bonds with just the polymer backbone of the water-swellable polymer material. In further embodiments, the microbead material may generally surround the one or more diamagnetic materials, yet the one or more diamagnetic materials may be covalently bonded to a functional group of the water-swellable polymer material.

In some embodiments, one or more diamagnetic materials may be incorporated into the microspheres to produce a loaded resin material. A loaded resin material may refer to a microbead material that includes the one or more diamagnetic materials physically disposed within a matrix, network, or pore structure throughout the microsphere material. In some specific embodiments, the loaded resin material may be a graphite-loaded material or a bismuth-loaded material.

In embodiments of incorporating the one or more diamagnetic materials into the microspheres, the microspheres may have a core-shell morphology, where the shell includes the microbead material, and the core, encapsulated by the shell, includes the one or more diamagnetic materials or the loaded resin material. The term "encapsulated" broadly includes embodiments for which the shell or some portion thereof generally surrounds the core. In some specific embodiments, where the microspheres have a core-shell morphology, the shell includes polycarbonate or nylon, and the core includes the loaded resin material. In other embodiments, the one or more diamagnetic materials or the loaded resin material may be the core material encapsulated in a biocompatible resin shell. Examples of the biocompatible resin may include, without limitation, epoxy resins, polyether ether ketone resins, high-density polyethylenes, or combinations thereof. In some embodiments, the biocompatible resin material may be used to separate the one or more diamagnetic materials or the loaded resin material from one or more other functional layers in the microbead. The microspheres having a core-shell morphology may be produced by a microfluidic manufacturing process. In other embodiments, the loaded resin material may be physically disposed within a matrix, network, or pore structure of the microbead material that may or may not have a core within an outer shell.

In embodiments, the plurality of microspheres may include one or more drug-loaded microspheres. In some embodiments, the plurality of microspheres may be entirely made up of drug-loaded microspheres, where each microbead also includes a diamagnetic material. In other embodiments, the plurality of microspheres may include a mixture of drug-loaded microspheres and microspheres that include a diamagnetic material.

In embodiments, the drug-loaded microspheres may be microspheres loaded with a therapeutic agent or with a complex of a therapeutic agent and a carrier. Individual drug-loaded microspheres of the plurality of microspheres may include one therapeutic agent or a plurality of therapeutic agents. Collectively, the microspheres of the plurality of microspheres may include some drug-loaded microspheres loaded with one specific therapeutic agent or a combination of specific therapeutic agents and other microspheres loaded with a different specific therapeutic agent or combination of specific therapeutic agents.

In some embodiments, the therapeutic agent may be a hydrophilic therapeutic agent, a water-soluble therapeutic agent, or a therapeutic agent that has at least some solubility in an aqueous solution. In some embodiments, the therapeutic agent may be a chemotherapeutic agent having at least some efficacy for treating a disease such as cancer. In some embodiments, the therapeutic agent may be a chemotherapeutic agent having at least some efficacy for treating a cancer such as hepatocellular carcinoma, liver cancer, prostate cancer, or breast cancer. The therapeutic agent may have one or more chemical moieties or atomic centers having a positive or negative charge or affinity. Examples of specific therapeutic agents may include, without limitation, doxorubicin, sorafenib, vandetanib, nivolumab, ipilimumab, regorafenib, irinotecan, epirubicin, pirarubicin, 5-fluorouracil, cisplatin, floxuridine, mitomycin C, derivatives of any of the foregoing, prodrugs of any of the foregoing, therapeutically acceptable salts or crystalline forms of any of the foregoing, or combinations of any of the foregoing. Further examples of suitable therapeutic agents include, without limitation, pirarubicin, mitoxantrone, tepotecan, paclitaxel, carboplatin, pemetrexed, penistatin, pertuzumab, trastuzumab, and docetaxel.

In some embodiments, the therapeutic agent may be a radiotherapeutic agent having at least some efficacy for treating a disease such as cancer. In some embodiments, the therapeutic agent may be a radiotherapeutic agent having at least some efficacy for treating a cancer such as hepatocellular carcinoma, liver cancer, prostate cancer, or breast cancer. The radiotherapeutic agent may include a radioisotope such as a beta-gamma emitter that emits sufficient gamma radiation to enable imaging. Examples of specific radiotherapeutic agents include, without limitation, bismuth-213, boron-10, cesium-131, cesium-137, cobalt-60, dysprosium-165, erbium-169, holmium-166, iodine-125, iodine-131, iridium-192, iron-59, lead-212, lutetium-177, molybdenum-99, palladium-103, phosphorus-32, potassium-42, radium-223, rhenium-186, rhenium-188, samarium-153, selenium-75, sodium-24, strontium-89, technetium-99m, thorium-227, xenon-133, ytterbium-169, ytterbium-177, and yttrium-90. Some other examples include actinium-225, astatine-211, bismuth-213, carbon-11, nitrogen-13, oxygen-15, fluorine-18, cobalt-57, copper-64, copper-67, fluorine-18, gallium-67, gallium-68, germanium-68, indium-111, iodine-123, iodine-124, krypton-81m, rubidium-82, strontium-82, and thallium-201. In some specific embodiments, the plurality of microspheres may include drug-loaded microspheres comprising yttrium-90.

In some embodiments, the water-swellable polymer material or some portion thereof generally surrounds the therapeutic agent or the complex including the therapeutic agent. In some embodiments, a water-soluble polymer material shell may encapsulate a core that holds the therapeutic agent or complex. In other embodiments, the therapeutic agent or the complex may be physically disposed within a matrix, network, or pore structure of a water-swellable polymer material that may or may not have a core within an outer shell.

In some embodiments, the therapeutic agent of the drug-loaded microbead may generally surround the microspheres of the microbead material but lack of covalent chemical bonds between the therapeutic agent and the microbead material. Despite lacking covalent chemical bonds, the therapeutic agent and microbead material may have noncovalent intermolecular interactions such as ionic interactions or a van der Waals interaction. In some embodiments, the therapeutic agent of the drug-loaded microbead may generally surround the microbead material and lack covalent chemical bonds to the polymer backbone water-swellable polymer material, yet the therapeutic agent may be chemically bonded to a functional group of the water-swellable polymer material. In some embodiments, the therapeutic agent is not chemically bonded to the water-swellable polymer material at all.

The drug-loaded microspheres may include an amount of therapeutic agent that has a desired therapeutic effect or activity, based on the intended use for the plurality of microspheres and the particular therapeutic agent present in the individual microspheres. The amount of therapeutic agent in the individual drug-loaded microspheres of the plurality of microspheres may be adjusted through particular techniques involved during drug loading, such as loading time, loading temperature, or concentration of therapeutic agent in a loading solution, for example. The amount of therapeutic agent in the individual drug-loaded microspheres of the plurality of microspheres may be adjusted through synthetic techniques involved for synthesizing the microspheres themselves, such as through adjusting polymer molecular weights, degree of hydrogel crosslinking, polymer density, or polymer porosity of the water-swellable polymer material. For example, when doxorubicin is the therapeutic agent, the amount of drug loading in the drug-loaded microspheres may be adjusted with respect to the number of negative charges in the polymer backbone of the water-swellable polymer material. Similarly, when sorafenib is the therapeutic agent, the sorafenib may be embedded within polymeric micelles or liposomes that may be embedded within the microbead structure. In some embodiments, the amount of therapeutic agent in the individual microspheres of the drug-loaded microspheres may be adjusted through choice of the carrier.

In some embodiments, when the therapeutic agent is a radiotherapeutic agent, the radiotherapeutic agent may be loaded into the microspheres by a precipitation method. For example, when yttrium-90 is the therapeutic agent, such precipitation methods may include preparing a solution of soluble yttrium salt (e.g., $YCl_3$) for which at least a portion of the yttrium is yttrium-90, chemically converting the soluble salt to small precipitates of an insoluble salt such as yttrium phosphate ($YPO_4$), adding microspheres to solution containing the precipitates, and causing the yttrium phosphate to nucleate onto the surfaces of the beads and, if the microbead is porous, into at least some of the pores. In another example, such precipitation methods may include adding microspheres to a solution of soluble yttrium (e.g., $YCl_3$) for which at least a portion of the yttrium is yttrium-90, allowing the soluble yttrium to penetrate into the pores of the microspheres, and then converting the soluble yttrium to insoluble yttrium, which may include yttrium phosphate ($YPO_4$), yttrium sulfate ($Y_2(SO_4)_3$), and yttrium carbonate ($Y_2(CO_3)_3$). In another example, yttrium-90 may be bonded to or coated onto surfaces of the microbead.

In example embodiments, the individual microspheres of the plurality of microspheres may include from about 1% by weight to about 25% by weight, or from about 1% by weight to about 20% by weight, or from about 1% by weight to about 15% by weight, or from about 2% by weight to about 25% by weight, or from about 5% by weight to about 25% by weight, or from about 10% by weight to about 25% by weight therapeutic agent, based on the total weight of the individual microspheres in the plurality of microspheres.

In some embodiments, the drug-loaded microbead may include a complex of a carrier and a therapeutic agent. In the complex, the therapeutic agent may be chemically bonded to the carrier or may be associated with the carrier by a noncovalent means such as encapsulation or a van der Waals interaction. In embodiments, the complex may be embedded within the microbead material. In further embodiments, the complex may be embedded within the water-swellable polymer material. When the complex is embedded within the microbead material, the carrier may be chemically bonded to the microbead material while the therapeutic agent is not chemically bonded to the microbead material. Without intent to be bound by theory, it is believed that when the therapeutic agent is bonded or associated with the carrier but is not chemically bonded to the microbead material, the drug-loaded microspheres of the plurality of microspheres may be less susceptible to shrinking as a result of replacing water molecules with drug molecules during drug loading. Accordingly, the final size distribution of the drug-loaded microspheres may be controlled more readily by selecting appropriate microbead sizes before the therapeutic agent is loaded.

In embodiments in which the drug-loaded microbead includes a complex of the carrier and the therapeutic agent, the carrier may be any pharmaceutically-acceptable compound that can complex with or encapsulate the therapeutic agent. In some embodiments, the carrier may have charged chemical groups or chemical groups with dipole moments that interact with corresponding chemical groups of the therapeutic agent having an opposite charge or opposite dipole moment. If the carrier is a polymeric material, the carrier may be a different material from the water-swellable polymer material. Non-limiting examples of suitable carriers include polysaccharides, liposomes, polymeric micelles, Pluronics, polycaprolactone-b-methoxy-PEG, poly(aspartic acid)-b-PEG, poly(benzyl-L-glutamate)-b-PEG, poly(D,L-lactide)-b-methoxy-PEG, poly(β-benzyl-L-asparate)-b-PEG). Non-limiting examples of polysaccharides include dextrans and dextran sulfates such as dextran sodium sulfate. In one example embodiment, the carrier may include a dextran sodium sulfate having a weight-average molecular weight of from about 40 kDa (kilodalton) to about 500 kDa, or from about 50 kDa to about 300 kDa, or from about 100 kDa to about 300 kDa, or about 100 kDa to about 200 kDa.

In example embodiments, the individual microspheres of the plurality of microspheres may include from about 1% by weight to about 40% by weight, or from about 1% by weight to about 30% by weight, or from about 1% by weight to about 25% by weight, or from about 1% by weight to about 20% by weight, or from about 5% by weight to about 40% by weight, or from about 10% by weight to about 40% by weight, or from about 20% by weight to about 40% by weight carrier, based on the total weight of the individual microbead in the plurality of microspheres.

In example embodiments, the individual microspheres of the plurality of microspheres include water. In example embodiments, the individual microspheres of the plurality of microspheres according to embodiments may have a low water content such as less than 1% by weight, or less than 0.5% by weight, or less than 0.1% by weight, or less than 0.05% (500 ppm) by weight, or less than 0.02% (200 ppm) by weight, or less than 0.01% (100 ppm) by weight, or less than 0.005 (50 ppm) by weight, or less than 0.002% (20 ppm) by weight, or less than 0.001% (10 ppm) by weight water, based on the total weight of the individual microspheres. Without intent to be bound by theory, it is believed that a low water content of the microbead increases the shelf-life and long-term stability of the microbead. Further, it is believed that water contents significantly greater than 1% by weight (such as 2%, 3%, 5%, or 10%, for example) based on the total weight of the microbead, may lead to decomposition or hydrolysis of the therapeutic agent, instability or breaking apart of the water-swellable polymer, or a combination of these, within a few days or even a few hours, such that the microbead cannot be used for embolization procedures, even if the microbead is rehydrated. It is believed that the shelf-life and long-term stability of having water contents significantly greater than 1% by weight are not sufficiently long to ensure viability of the therapeutic agent over the time period from manufacture of the microbead to use of the in an embolization procedure. It is believed that selection of the water-swellable polymer material may correlate with the ability for water to be removed from the microspheres by lyophilization or other drying technique or combination of drying techniques in an amount sufficient to prevent decomposition of the therapeutic agent.

A low water content of the microbead, as previously described, may be attained by drying techniques. In this regard, the microspheres may be dry or nearly dehydrated compositions of the microspheres containing the embedded therapeutic agent or the embedded complex of the therapeutic agent and the carrier. The microspheres may have a powder-like consistency. Accordingly, the microspheres may be made suitable for injection into a subject being treated by rehydrating the microspheres so that the plurality of microspheres may be suitable for embolization. Regardless, the microspheres may be provided in such a form that a physician needs to add only an aqueous solution such as water or physiologically buffered saline solution to the plurality of microspheres to prepare the plurality of microspheres for use in an embolization procedure.

The present disclosure includes one or more non-limiting aspects. A first aspect may include a flaring tip microcatheter, the microcatheter comprising: a hollow shaft having a shaft lumen defined therein; a core disposed within the shaft lumen, wherein the core is hollow and defines a core lumen; a tip comprising at least two petals affixed to a distal end of the core, the at least two petals comprising at least two wires, wherein: the at least two wires are configured to pull the at least two petals to form a flared configuration of the tip; and the flared configuration of the tip allows for laminar flow of a therapeutic agent distally from the tip.

A second aspect may include the first aspect, wherein the at least two wires are disposed between the core and the shaft within the shaft lumen.

A third aspect may include any preceding aspect, wherein each petal of the at least two petals comprise one wire.

A fourth aspect may include any preceding aspect, further comprising a slide, wherein the at least two wires are affixed to the slide, and wherein the slide is configured to pull the at least two wires.

A fifth aspect may include any preceding aspect, wherein the at least two petals overlap at a seam.

A sixth aspect may include any preceding aspect, wherein the at least two wires extend straight along a horizontal axis of the microcatheter.

A seventh aspect may include any preceding aspect, wherein the at least two wires intertwine around the core in a braided manner along the horizontal axis of the microcatheter.

An eighth aspect may include any preceding aspect, further comprising at least four petals.

A ninth aspect may include any preceding aspect, wherein the slide is configured to flare the at least two petals when pulled.

A tenth aspect may include any preceding aspect, wherein each petal of the at least two petals comprises two or more wires.

An eleventh aspect may include any preceding aspect method of deploying a flaring tip microcatheter, the method comprising advancing a flaring tip microcatheter having a proximal end and a distal end through a vessel, the flaring tip microcatheter comprising a hollow shaft having a shaft lumen defined therein; a core disposed within the shaft lumen, wherein the core is hollow and defines a core lumen; and a tip comprising at least two petals affixed to a distal end of the core, wherein the at least two petals comprise at least two wires; pulling the at least two wires to flare the at least two petals and form a flared configuration of the tip, wherein the flared configuration of the tip allows for laminar flow of a therapeutic agent distally from the tip.

A twelfth aspect may include the eleventh aspect, wherein the flaring tip microcatheter further comprises a slide affixed to the at least two wires, and wherein the slide is configured to pull the at least two wires.

A thirteenth aspect may include the twelfth aspect, wherein pulling the at least two wires may further include pulling the slide affixed to the at least two wires.

A fourteenth aspect may include the eleventh through thirteenth aspects, further comprising advancing a guidewire through the core lumen, and guiding the guidewire through a vessel within a body.

A fifteenth aspect may include the fourteenth aspect, wherein the therapeutic agent comprises radiotherapeutic agent, chemotherapeutic agent, or combinations thereof.

A sixteenth aspect may include the fifteenth aspect, wherein the therapeutic agent comprises radiotherapeutic microspheres, chemotherapeutic micro spheres, or combinations thereof.

A seventeenth aspect may include an embolization treatment method, the method comprising: advancing a flaring tip microcatheter having a proximal end and a distal end through a vessel within the body of patient, the flaring tip microcatheter comprising: a hollow shaft having a shaft lumen defined therein; a core disposed within the shaft lumen, wherein the core is hollow and defines a core lumen; and a tip comprising at least two petals affixed to a distal end of the core, wherein the at least two petals comprise at least two wires; pulling the at least two wires to flare the at least two petals and form a flared configuration of the tip, whereby the flared configuration of the tip allows for laminar flow of a therapeutic agent distally from the tip; and delivering a therapeutic agent to the vessel within the body of the patient comprising expelling the therapeutic agent from the distal end of the flaring tip microcatheter through the core lumen.

A eighteenth aspect may include the seventeenth aspect, wherein the therapeutic agent comprises radiotherapeutic agent, chemotherapeutic agent, or combinations thereof.

A nineteenth aspect may include the seventeenth through eighteenth aspects, wherein the therapeutic agent comprises radiotherapeutic microspheres, chemotherapeutic microspheres, or combinations thereof.

A twentieth aspect may include the seventeenth through nineteenth aspects, further comprising pulling a slide affixed to the at least two wires, wherein the slide is configured to pull the at least two wires.

For the purposes of describing and defining the present disclosure it is noted that the term "substantially" is used herein to represent the inherent degree of uncertainty that may be attributed to any quantitative comparison, value, measurement, or other representation. The term "substantially" is used herein also to represent the degree by which a quantitative representation may vary from a stated reference without resulting in a change in the basic function of the subject matter at issue. As such, it is used to represent the inherent degree of uncertainty that may be attributed to any quantitative comparison, value, measurement, or other representation, referring to an arrangement of elements or features that, while in theory would be expected to exhibit exact correspondence or behavior, may in practice embody something slightly less than exact.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. A flaring tip microcatheter, the microcatheter comprising:
   a hollow shaft having a shaft lumen defined therein;
   a core disposed within the shaft lumen, wherein the core is hollow and defines a core lumen;
   a tip comprising at least two petals affixed to a distal end of the core, the at least two petals comprising at least two wires;
   wherein:
   the at least two wires are configured to pull the at least two petals to form a flared configuration of the tip with a distal flared opening of the tip larger than a proximal diameter of the tip; and
   the flared configuration of the tip allows for laminar flow of a therapeutic agent distally from the tip.

2. The microcatheter of claim 1, wherein the at least two wires are disposed between the core and the shaft within the shaft lumen.

3. The microcatheter of claim 1, wherein each petal of the at least two petals comprises one wire.

4. The microcatheter of claim 1, further comprising a slide, wherein the at least two wires are affixed to the slide, and wherein the slide is configured to pull the at least two wires.

5. The microcatheter of claim 4, wherein the slide is configured to flare the at least two petals when the at least two wires are pulled.

6. The microcatheter of claim 1, wherein the at least two petals overlap at a seam.

7. The microcatheter of claim 1, wherein the at least two wires extend straight along a longitudinal axis of the microcatheter.

8. The microcatheter of claim 1, wherein the at least two wires intertwine around the core in a braided manner along the longitudinal axis of the microcatheter.

9. The microcatheter of claim 1, comprising at least four petals.

10. The microcatheter of claim 1, wherein the tip is a radiopaque tip.

11. The microcatheter of claim 1, wherein the at least two petals are in a row, further comprising one or more additional rows of petals.

* * * * *